United States Patent [19]

Minowa et al.

[11] Patent Number: 5,194,617
[45] Date of Patent: Mar. 16, 1993

[54] 2,3-DISUBSTITUTED-4-HYDROXYQUINOLINE DERIVATIVES

[75] Inventors: Nobuto Minowa; Tomoya Machinami; Takashi Shomura; Masaji Sezaki; Toru Sasaki; Seiji Shibahara; Shigeharu Inouye, all of Yokohama, Japan

[73] Assignee: Meiji Seika Kaisha, Ltd., Tokyo, Japan

[21] Appl. No.: 807,946

[22] Filed: Dec. 10, 1991

Related U.S. Application Data

[63] Continuation of Ser. No. 449,012, Dec. 11, 1989, abandoned.

[30] Foreign Application Priority Data

Dec. 17, 1988 [JP] Japan .................. 63-319231

[51] Int. Cl.$^5$ .................................. C07D 215/22
[52] U.S. Cl. .................................... 546/153
[58] Field of Search ................ 514/312; 546/153

[56] References Cited

U.S. PATENT DOCUMENTS

| | | | |
|---|---|---|---|
| 3,301,859 | 1/1967 | Cheney et al. | 546/153 |
| 4,301,291 | 11/1981 | Leir | 546/153 |

FOREIGN PATENT DOCUMENTS

0374765  6/1990  European Pat. Off. ............ 546/153

OTHER PUBLICATIONS

Homma et al. Ann. Phytopath. Soc. Japan vol. 55 pp. 643–652 (1989).
Hashimoto et al. Chem. Pharm Bull. vol. 15 pp. 718–720 (1967).
Homma et al. Soc. Biol. Biochem. vol. 21 No. 5 pp. 723–728 (1989).
Wells, J. Biol. Chem. vol. 196, 331–40 (1952).
Wells et al., J. Biol. Chem. vol. 196, 321–330 (1952).
Kan-Fan et al., Phytochem. vol. 9, pp. 1283–1291 (1970).
Hauser et al., Jour. Am. Chem. Soc. vol. 70, pp. 2402–2403 (1948).
Chong et al., Tetrahed. Lett. vol. 27 5323–26 (1986).
Fleming et al., Jour. Chem. Soc. 1970, 2426–8.
Ash et al., Jour. Het. Chem. vol. 18, 939–40 (1981).
Caldwell, Jour. Chem. Soc., 1952, pp. 2035–2041.
Hays et al., Jour. Biol. Chem. vol. 159, 725–750 (1945).
Homma et al., Chem. Abstr. vol. 111, entry 228636h (1989).

*Primary Examiner*—Donald G. Daus
*Attorney, Agent, or Firm*—Jordan and Hamburg

[57] ABSTRACT

2,3-disubstituted-4-hydroxyquinoline derivatives of the general formula (I):

[wherein $R^1$ represents a hydrogen atom or $R^3CO-$ (wherein $R^3$ is a lower alkyl group); $R^2$ represents a hydrogen atom, $-CH_3$ or $-C_2H_5$; A represents $$-CH_2CH=CH-,\quad -\underset{\underset{OH}{|}}{C}HCH=CH-,\quad -\underset{\underset{OH}{|}}{C}HC\equiv C-$$

$-CH=CHCH_2-$ or $CH_2C\equiv C-$;

and W represents a hydrogen atom, or 1–4 halogen atoms or alkyl groups which are substituted at the nucleus and may be the same or different] have a strong antagonistic action on leukotriene $D_4$.

1 Claim, No Drawings

2,3-DISUBSTITUTED-4-HYDROXYQUINOLINE DERIVATIVES

This application is a continuation of application Ser. No. 07/449,012, filed Dec. 11, 1989, abandoned.

BACKGROUND OF THE INVENTION

1. Field of the Invention

This invention relates to novel 4-hydroxyquinoline derivatives which have been found during the course of systematic studies of 2,3-disubstituted-4-hydroxyquinoline derivatives and which have antagonistic action on leukotriene $D_4$ and also to a process for chemically preparing the same. The novel 2,3-disubstituted-4-hydroxyquinoline derivatives of the invention strongly antagonize leukotriene $D_4$ which is energized in the body of mammals in an allergic state and has the action of shrinking organs and are thus useful for curing allergic diseases and particularly, asthma.

2. Description of the Prior Art

Several 2,3-disubstituted-4-hydroxyquinolines have been heretofore isolated as metabolites from microorganisms such as Pseudomonas pyocyaneum [*Journal of Antibiotics* (J. A.) 39, 1160 (1986) and *Chemical Pharmaceutical Bulletin* 15, 718 (1967)]. However, some of these compounds have the disadvantage that the production efficiency by microorganism fermentation is very low and their invariable supply is difficult in some cases.

Several 2,3-disubstituted-hydroxyquinoline compounds having an unsaturated hydrocarbon chain at the 2 position are known including 2-(1-heptenyl)-4-quinolone [*Journal of Biological Chemistry* 159, 725 (1945)], 2-(2-heptenyl)-3-methyl-4-quinolone, 2-(3,6-nonadienyl)-4-quinolone [*Chemical Pharmaceutical Bulletin* 15, 718 (1967)], and 2-(4-heptenyl)-4-quinolone (*Phytochemistry* 9, 1283 (1970)].

However, no effective process of preparing 2, 3-disubstituted-4-hydroxyquinoline having an alkyl, alkenyl or alkynyl group at the 2 or 3 position has ever been known up to now.

Moreover, it is known that among the 3-substituted-4-hydroxyquinoline derivatives isolated as a metabolite of microorganism, those having a residue of acrylic acid or its ester at the 3 position are antagonistic against leukotriene $D_4$, but their activity is generally weak (European Patent Publication No. 55068). The 4 quinolone compounds isolated as the metabolite of a microorganism have an alkyl or alkenyl group having 7-9 carbon atoms at the 2 or 3 position.

SUMMARY OF THE INVENTION

It is an object of the invention to provide novel 2, 3-disubstituted-4-hydroxyquinoline derivatives which have higher antagonistic action on leukotriene $D_4$ than known 4-quinolone compounds.

It is another object of the invention to provide a process for preparing a series of compounds including the metabolites of a microorganism and its analogues through chemical reactions.

It is a further object of the invention to provide a process for preparing novel 2, 3-disubstituted-4-hydroxyquinoline derivatives which have higher antagonistic action on leukotriene $D_4$ than known 4-quinolone compounds.

According to the invention, there is provided a 2, 3-disubstituted-4-hydroxyquinoline derivative of the general formula (I):

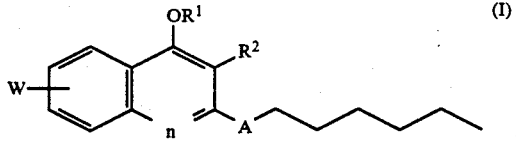

[wherein $R^1$ represents a hydrogen atom or $R^3CO-$ (wherein $R^3$ is a lower alkyl group); $R^2$ represents a hydrogen atom, $-CH_3$ or $-C_2H_5$; A represents

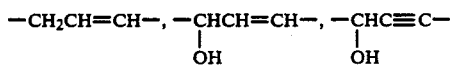

and W represents a hydrogen atom, or halogen atoms or alkyl groups which are substituted at the nucleus and may be the same or different]. having strong antagonistic action on leukotriene $D_4$ and there is also provided a process for preparing such a derivative as defined above and analogous compounds thereof.

DESCRIPTION OF THE PREFERRED EMBODIMENTS

The 2, 3-disubstituted-4-hydroxyquinoline derivatives of the general formula (I) having physiological activity wherein $R^1$ is a hydrogen is a tautomer relative to the 2, 3-disubstituted-4-quinolone derivative of the formula (VIII):

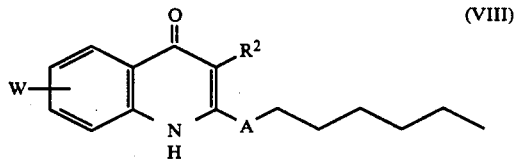

wherein $R^2$, A and W have, respectively, the same meanings as defined before. As a matter of course, the compound of the formula (VIII) is also within the scope of the invention.

Examples of the 2, 3-disubstituted-4-hydroxyquinoline derivative according to the invention include:
2-(trans-1-nonenyl)-3-methyl-4-acetoxyquinoline,
2-(trans-1-nonenyl)-3-methyl-4-quinolone,
2-(cis-1-nonenyl)-3-methyl-4-acetoxyquinoline,
2-(cis-1-nonenyl)-3-methyl 4-quinolone,
2-(trans-2-nonenyl)-3-methyl-4-acetoxyquinoline,
2-(trans-2-nonenyl)-3-methyl-4-quinolone,
2-(1-hydroxy-2-nonynyl)-3-methyl-4-acetoxyquinoline,
2-(1-hydroxy-2-nonynyl)-3-methyl-4-quinolone,
2-(trans-1-hydroxy-2-nonynyl)-3-methyl-4-acetoxyquinoline,
2-(trans-1-hydroxy-2-nonynyl)-3-methyl-4-quinolone,
2-(trans-2-nonenyl)-3-methyl-4-propionyloxyquinoline,
2-(trans-1-nonenyl)-3-methyl-4-propionyloxyquinoline,
2-( trans-1-hydroxy -2-nonenyl)-3-methyl-4-propionyloxyquinoline,
2-(trans-2-nonenyl)-3-methyl-4-butyryloxyquinoline,
2-(trans 1 nonenyl)-3-methyl-4-butyryloxyquinoline,
2-(1-hydroxy-2-nonynyl)-3-methyl-4-butyryloxyquinoline
2-(trans-2 nonenyl)-3-ethyl-4-acetoxyquinoline,
2-(trans-1-nonenyl)-3-ethyl-4-acetoxyquinoline 2-(trans-1-hydroxy-2-nonynyl)-3-ethyl-4-acetoxyquinoline,
2-(1-hydroxy-2-nonenyl)-3-ethyl-4-acetoxyquinoline,
2-(trans-2-nonenyl)-3-ethyl-4-propionyloxyquinoline,
2-(trans-1-nonenyl)-3-ethyl-4-propionyloxyquinoline,
2-(trans-2-nonenyl)-3-ethyl 4-butyryloxyquinoline,
2-(trans-1-nonenyl)-3-ethyl-4-butyryloxyquinoline,
2-(trans-2-nonenyl)-3-ethyl-4-quinolone,
2-(trans-1-nonenyl)-3-ethyl-4-quinolone,
2-(trans-1-hydroxy-2-nonenyl)-3-ethyl 4-quinolone,
2-(1-hydroxy-2-nonynyl)-3-ethyl-4-quinolone,
2-(trans-1-nonenyl)-3-methyl-4-acetoxy-6-fluoroquinoline,
2-(trans-1-nonenyl)-3-methyl-6-fluoro-4-quinolone,
2-(trans-2-nonenyl)-3-methyl-4-actoxy-6-fluoroquinoline,
2-(trans-2-nonenyl)-3 methyl-6-fluoro-4-quinolone,
2 (1-hydroxy-2-nonynyl)-3-methyl-4-actoxy-6-fluoroquinoline, 2-(1-hydroxy-2-nonynyl)-3-methyl-4-acetoxy-6-fluoroquinoline, 2-(1-hydroxy-2-nonynyl)-3-methyl-6-fluoro-4-quinolone, 2-(trans-1-hydroxy-2-nonenyl)-3-methyl-4-acetoxy-6-fluoroquinoline, 2-(trans-1-hydroxy-2-nonenyl)-3-methyl-6-fluoro-4-quinolone, 2-(trans-1-nonenyl)-3-methyl-4-acetoxy-6-methylfluoroquinoline, and the like.

For the preparation of the 2, 3-disubstituted-4-hydroxyquinoline derivatives of the invention wherein the substituent at the 2-position is a 1-hydroxy-2-nonenyl group or a 1-hydroxy-nonynyl group represented by the following formula (IV):

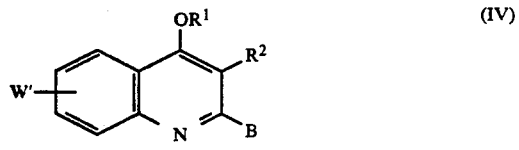

(wherein B represents

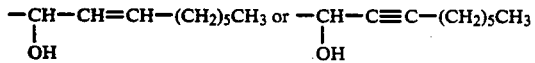

$R^1$ and $R^2$ have, respectively, the same meanings as defined before, and W' represents a hydrogen atom or 1–4 halogen atoms, alkyl groups, alkoxy groups or acyl groups which are substituted at the nucleus and may be the same or different), there are reacted a compound of the general formula (II):

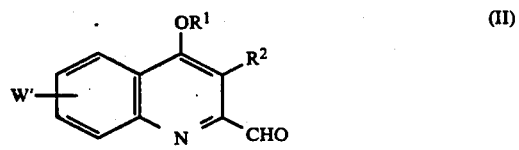

(wherein $R^1$, $R^2$ and W' have, respectively, the same meanings as defined before), and a compound of the general formula (III),

[wherein Y represents Li, Na, K, Mg, LiCu, $R^4{}_2$Al or $R^4$CuLi (wherein $R^4$ represents an alkyl or alkenyl group having 1–8 carbon atoms), Z represents —CH═CH— or —C≡C—, and n is a valence of the metal Y].

This reaction can be carried out by subjecting the compound of the general formula (II) to direct reaction with the compound of the general formula (III) including a metal alkene or metal alkyne such as, for example, octenyl lithium, octynyl lithium, lithium di(octenyl)cuprate, lithium di(octynyl)cuprate, lithium octenylmethylcuprate, lithium octynylmethyl cuprate and the like, in an ether solvent at a temperature from room temperature to −20° C. Alternatively, the reaction may be carried out after reaction in the above-indicated solvent between octene or octyne and a metal hydride such as, for example, sodium hydride, potassium hydride or the like, a metal alkoxide such as potassium butoxide, magnesium ethoxide, a Grignard reagent, diisobutylaluminum hydride, butyl lithium or the like to form a metal alkene or metal alkyne in the reaction solution.

By the above reaction, the compound of the general formula (IV) can be prepared.

For the preparation of the 2,3-disubstituted-4-hydroxyquinoline derivatives of the present invention wherein the substituent at the 2 position is a 1-nonenyl group, i.e., the compound of —CH═CH(CH$_2$)$_6$CH$_3$ represented by the following general formula (V):

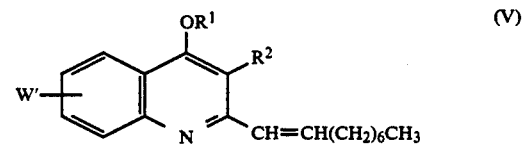

(wherein $R^1$, $R^2$ and W' have, respectively, the same meanings as defined before), the compound of the general formula (II) and a compound of the following formula:

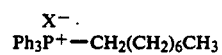

(wherein X represents a halogen atom, and Ph represents a phenyl group) are subjected to the ordinary Wittig reaction. It is preferred that the phosphonium salt is treated with an inorganic base such as, for example, sodium hydride, butyl lithium or the like, for conversion to a corresponding ylide which is used for the above reaction.

For the preparation of the 2, 3-disubstituted-4-hydroxyquinoline derivatives of the present invention wherein the substituent at the 2 position is 2-nonenyl group or 2-nonynyl group, i.e., the compound of —CH$_2$—CH═CH (CH$_2$)$_5$CH$_3$ or —CH$_2$—C≡C(CH$_2$)$_5$CH$_3$ represented by the following general formula (VII):

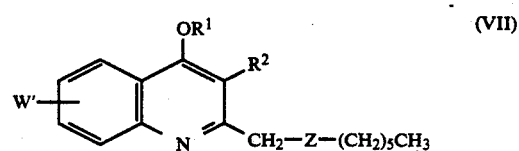

(wherein $R^1$, $R^2$, W' and Z have, respectively, the same meanings as defined before), there are reacted the compound of the general formula (VI):

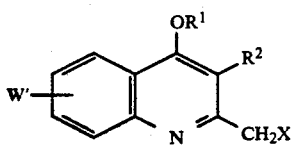

(wherein X, R¹, R² and W' have, respectively, the same meanings as defined before), and the compound of the general formula (III),

(wherein Y, Z and n have, respectively, the same meanings as defined before).

The compound represented by the general formula (III) and reaction conditions used for the above preparation are similar to those used for the reaction of the compound of the general formula (II) and the compound of the general formula (III) set out before.

In the process of the invention, the 3-methyl substituted compound among the starting 2-formyl-3-substituted-4-(hydroxy or acyloxy) quinoline derivatives represented by the general formula (II) can be prepared by subjecting aniline to dehydration condensation with ethyl 2-methylacetoacetate to form a 3-anilino-2-methylcrotonic acid derivative, followed by intramolecular cyclization by heating to high temperature of, preferably, 200° to 250° C. to obtain 2, 3-dimethyl-4-quinoline. Moreover, this compound may further reacted with an anhydrous alkanoic acid such as, for example, acetic anhydride, to obtain 2, 3-dimethyl-4-acyloxyquinoline, e.g. 2, 3-dimethyl-4-acetoxyquinoline, followed by oxidation with selenium dioxide in an aqueous organic solvent to obtain the derivative.

Another starting compound used in the process of the invention which is the 2 halogenomethyl-3, 4-disubstituted hydroxyquinoline derivative represented by the general formula (VI) can be prepared by oxidizing the above-obtained 2, 3-dimethyl-4-quinoline with m-chloroperbenzoic acid in an organic solvent to obtain a 4-acyloxyquinoline-N-oxide derivative, followed by chlorination with phosphorus oxychloride in a nonaqueous organic solvent to obtain 2-chloromethyl-3-methyl-4-acyloxyquinoline.

For the conversion of the chloromethyl group at the 2 position to another halogenomethyl group, the above-obtained 2-chloromethyl-3-methyl-4-acyloxyquinoline is reacted with sodium iodide or sodium bromide in an aqueous solvent in the preparation.

The 2, 3-disubstituted-4-hydroxyquinoline derivatives of this invention are substances which show physiological activity on the immune system and cardiac blood system which are important for life conservation of mammals including human beings. As an influence on the immune system, the antagonistic action on leukotriene D₄ is very remarkable.

The present invention is described in more detail in the following examples and preparatory examples for starting compounds.

EXAMPLE 1

2-(1-nonenyl)-3-methyl-4-acetoxyquinoline 0.29 ml of a hexane solution of 0.48 mmols of n-butyl lithium was added to a solution of 218 mg (0.48 mmols) of octyltriphenylphosphonium bromide in 3 ml of tetrahydrofuran and stirred at room temperature for 5 minutes.

This solution was cooled to −78° C., after which 1.43 g (8 mmols) of hexamethylphosphorus triamide was added and stirred for 5 minutes, followed by further addition of 2 ml of a tetrahydrofuran solution of 91.6 mg (0.40 mmols) of 2-formyl-3-methyl-4-acetoxyquinoline and stirring at −78° C. for 15 minutes and subsequently at −42° C. for 30 minutes. The reaction mixture was added to 20 ml of water and extracted with ethyl acetate, followed by washing with a saturated sodium chloride aqueous solution and drying with sodium sulfate. After removal of the solvent by distillation under reduced pressure, the residue was purified by silica gel column chromatography [Wako Gel C-200 (available from Wako Junyaku Co., Ltd.) (solvent n-hexane : ethyl acetate=15:1)] to obtain 13 mg of 2-(trans-1-nonenyl)-3-methyl-4-acetoxyquinoline (yield 10%) and 15 mg of 2-(cis-1-nonenyl)-3-methyl-4-acetoxyquinoline (yield 12%).

2-(trans-1-nonenyl)-3-methyl 4-acetoxyquinoline

Compound (1)

Melting point 74°–75° C.
NMR (CDCl₃).
$\delta=0.90$ (t, J=7Hz, 3H), 1.2–1.5 (m, 10H), 2.31 (s, 3H), 2.33–2.40 (m, 2H), 2.51 (s, 3H), 6.80 (d, J=15.4Hz, 1H), 7.08 (dt, J=15.4Hz, J=7.1Hz, 1H), 7.4–7.8 (m, 3H), 8.04 (d, J=8.8Hz, 1H).

2-(cis-1-nonenyl)-3-methyl-4-acetoxyquinoline

Compound (2)

MMR (CDCl₃).
$\delta=0.84$(t, J=6Hz, 3H), 1.1–1.6 (m, 10H), 2.2–2.7 (m, 2H), 2.26 (s, 3H), 2.49 (s, 3H), 6.02 (dt, J=12Hz, J=7Hz, 1H), 6.61 (d, J=12Hz, 1H), 7.3–8.1 (m, 4H).

EXAMPLE 2

2 (trans 1-nonenyl) 3-methyl 4 quinolone [Compound (3)]

30 ml of an aqueous solution of 6.30 g (45.6 mmols) of potassium carbonate was added to a solution of 2.47 g (7.60 mmols) of 2-(trans-1-nonenyl)-3-methyl-4-acetoxyquinoline, 250 ml of methanol and 50 ml of water and stirred at room temperature for 13 hours. This solution was neutralized with 1N hydrochloric acid, after which the solvent was distilled off under reduced pressure, to which 100 ml of chloroform was added, followed by washing with water and drying with sodium sulfate. The solvent was distilled off under reduced pressure and the resultant residue was purified by silica gel column chromatography (Wako Gel C-200) (solvent: n-hexane : ethyl acetate=1:2) to obtain 1.66 g (yield 77%) of 2-(trans-1-nonenyl)-3-methyl-4-quinolone.

Melting point 152°–153° C.
MS m/e 283(M+).
NMR (CDCl₃).
$\delta=0.86$ (t, J=7Hz, 3H), 1.1–1.5 (m, 10H), 2.13–2.19 (m, 2H), 2.22 (s, 3H), 6.56 (dd, J=16.02Hz, J=5.47Hz, 1H), 6.62 (d, J=16.02Hz, 1H), 7.22–7.26 (m, 1H), 7.49–7.54 (m, 1H), 7.70 (d, J=7.8Hz, 1H), 8.33–8.35 (m, 1H), 10.40 (bs, 1H).

EXAMPLE 3

2-(cis-1-nonenyl)-3-methyl-4-quinolone [Compound (4)]

205 mg (1.49 mmols) of potassium carbonate and 2 ml of water were added to a solution of 483 mg (1.49 mmols) of 2-(cis-1-nonenyl)-3-methyl-4-acetoxyquinoline, 1 ml of water and 30 ml of methanol and stirred at room temperature for 13 hours. Thereafter, the solution was treated and purified in the same manner as in Example 2 to obtain 360 mg (yield 86%) of 2-(cis-1-nonenyl)-3-mehtyl-4-quinolone.

Melting point 170°–171° C.

NMR (CDCl$_3$).

$\delta$=0.82 (t, J=6Hz, 3H), 1.0–1.5 (m, 10H), 2.06 (s, 3H), 2.07–2.30 (m, 2H), 5.89 (dt, J=12Hz, J=7.5Hz, 1H), 6.33 (d, J=12Hz, 1H), 7.1–7.6 (m, 2H), 8.33 (d, J=7.5Hz, 1H), 9.15 (bs, 1H).

EXAMPLE 4

2-(trans-2-nonenyl)3-methyl-4-acetoxyquinoline [Compound (5)]

10 ml of a pentane solution of 15.6 mmols of t-butyl lithium was added to 15 ml of 1.86 g (7.8 mmols) of trans-1-iodo-1-octene ether solution in an atmosphere of argon at −78° C. and stirred at the same temperature for 2 hours. The reaction solution was added to 15 ml of an ether solution of 590 mg (3.10 mmols) of copper iodide at −78° C., after which it was heated up to −35° C. and stirred at the same temperature for 45 minutes. 1.79 g (10 mmols) of hexamethylphosphorus triamide was added to the solution and stirred at −35° C. for 10 minutes, to which 10 ml of a tetrahydrofuran solution of 1.02 g (3.00 mmols) of 2-iodomethyl-3-methyl-4-acetoxyquinoline was added, followed by stirring at the same temperature for 30 minutes. The reaction solution was added to a solution of 3 ml of 1N hydrochloric acid and 100 ml of water, followed by filtration through Celite. The resultant filtrate was extracted with chloroform, washed with water and dried with sodium sulfate. The solvent was distilled off under reduced pressure and the residue was purified by silica gel column chromatography (Wako Gel C-200) (solvent: n-hexane : ethyl acetate=15:1) to obtain 221 mg (yield 23%) of 2-(trans-2-nonenyl)-3-methyl-4-acetoxyquinoline MS m/e 325 (M+).

$^1$HNMR (CDCl$_3$).

$\delta$=0.86 (t, J=6.94Hz, 3H), 1.23–1.36 (m, 8H), 2.01 (dt, J=6.66Hz, 2H), 2.28 (s, 3H), 2.50 (s, 3H), 3.75 (d, J=6.2Hz, 2H), 5.50 (dt, J=15.5Hz, J=6.66Hz, 1H), 5.86 (dt, J=15.5Hz, J=6.2Hz, 1H), 7.48 (t, J=8Hz, 1H), 7.64 (t, J=8.3Hz, 1H), 7.70 (d, J=8.3Hz, 1H), 8.05 (d, J=8.3Hz, 1H).

$^{13}$CNMR (CDCl$_3$).

$\delta$=12.23, 14.03, 20.52, 22.57, 28.80, 29.25, 31.67, 32.61, 40.74, 120.66, 121.43, 121.59, 125.77, 126.26, 128.90, 129.00, 133.10, 147.46, 151.90, 161.62, 167.92.

EXAMPLE 5

2 (trans-2-nonenyl)-3-methyl-4-quinolone [Compound (6)]

A solution of 300 mg (2.17 mmols) of potassium carbonate and 3 ml of water was added to a solution of 705 mg (2.17 mmols) of 2-(trans-2-nonenyl)-3-methyl-4-acetoxyquinoline, 10 ml of water and 50 ml of methanol and stirred at room temperature for 10 minutes. This solution was neutralized with 1N hydrochloric acid, after which the solvent was distilled off under reduced pressure, followed by addition of 50 ml of chloroform, washing with water and drying with sodium sulfate. The solvent was distilled off under reduced pressure and the resultant residue was purified by silica gel column chromatography (Wako Gel C 200) (solvent: n-hexane : ethyl acetate=1:2) to obtain 550 mg (yield 90%) of 2-(trans-2-nonenyl)-3-methyl-4-quinolone.

Melting point 202°–203° C.

MS m/e 283 (M+).

NMR (CDCl$_3$).

$\delta$=0.84 (t, J=6Hz 3H), 1.10–1.05 (m, 8H), 1.80–2.10 (m, 2H), 2.16 (s, 3H), 3.38–3.59 (m, 2H), 5.51 (dt, J=15.3Hz, J=6.5Hz, 1H), 5.61 (dt, J=15.3Hz, J=6.5Hz, 1H), 7.10–7.34 (m, 1H), 7.40–7.58 (m, 2H), 8.32 (d, J=8.4Hz, 1H), 10.70 (bs, 1H).

EXAMPLE 6

2-(1-hydroxy-2-nonynyl)-3-methyl-4-acetoxyquinoline [Compound (7)]

4.9 ml of a hexane solution of 8.00 mmols of n-butyl lithium was added to a solution of 968 mg (8.80 mmols) of 1-octyne in 10 ml of tetrahydrofuran in an atmosphere of nitrogen at 0° C. and stirred at the same temperature for 15 minutes. The reaction solution was cooled to −78° C., to which a solution of 10 ml of tetrahydrofuran of 1.83 g (8.00 mmols) of 2-formyl-3-methyl-4-acetoxyquinoline was added, following by heating gradually to room temperature and stirring at room temperature for 1 hour. The reaction solution was poured into 100 ml of water, extracted with ethyl acetate and dried with sodium sulfate. The solvent was distilled off under the reduced pressure and resultant residue was purified by silica gel column chromatography (Wako Gel C-200) (solvent: n-hexane ethyl acetate=2:1) to obtain 1.50 g (yield 55%) of 2-(1 hydroxy-2-nonynyl)-3-methyl-4-acetoxyquinoline.

NMR (CDCl$_3$).

$\delta$=0.86 (t, J=6Hz 3H), 1.15–1.65 (m, 8H), 2.16 (s, 3H), 2.20–2.40 (m, 2H), 6.60 (t, J=2Hz, 1H), 7.16–7.66 (m, 3H), 8.23 - 8.40 (m, 1H).

EXAMPLE 7

2-(1-hydroxy-2-nonynyl)-3-methyl-4-quinolone [Compound (8)]

A solution of 611 mg (4.42 mmols) of potassium carbonate in 2.0 ml of water was added to a solution of 1.50 g (4.42 mmols) of 2-(1-hydroxy-2-nonynyl)-3-methyl-4-acetoxyquinoline, 10 ml of water and 100 ml of methanol and stirred at room temperature for 10 minutes. After neutralization with 1N hydrochloric acid, the solvent was distilled off under reduced pressure, followed by addition of 30 ml of chloroform to the resultant residue, washing with water and drying with sodium sulfate. The solvent was distilled off under reduced pressure, followed by purification by silica gel column chromatography (Wako Gel C-200) (solvent: n-hexane : ethyl acetate=1:2) to obtain 945 mg (yield 72%) of 2 (1-hydroxy-2-nonynyl)-3-methyl-4-quinolone.

Melting point 148°–149° C.

MS m/e 297 (M+).

NMR (CDCl$_3$).

$\delta$=0.81 (t, J=6Hz 3H), 1.0–1.5 (m, 8H), 1.94 (s, 3H), 2.0–2.3 (m, 2H), 4.34 (bs, 1H), 5.49 (bs, 1H), 6.9–7.5 (m, 3H), 8.21 (d, J=8Hz, 1H), 9.01 (s, 1H).

EXAMPLE 8

2-(trans-1-hydroxy-2 nonenyl)-3-methyl-4-acetoxyquinoline [Compound (9)]

13.9 ml of an n-hexane solution of 13.9 mmols of diisobutylaluminium hydride was added to a solution of 1.68 g (1.53 mmols) of 1-octyne in 20 ml of n-hexane in an atmosphere of nitrogen at 0° C. and stirred at 50° C. for 2 hours. After removal of the solvent by distillation under reduced pressure, 20 ml of tetrahydrofuran was added, followed by further addition of a solution, in 15 ml of tetrahydrofuran, of 2.66 g (11.6 mmols) of 2-formyl-3-methyl 4-acetoxyquinoline at −78° C. The reaction temperature was raised from −78° C. to room temperature and the reaction solution was stirred at room temperature for 15 minutes. The solution was added to a solution of 15 ml of 1N hydrochloric acid and 100 ml of water and filtered through Celite, followed by extraction with ethyl acetate, washing with water and then with a saturated sodium chloride aqueous solution, and drying with sodium sulfate. The solvent was distilled off under reduced pressure and the resultant residue was purified by silica gel column chromatography (solvent: n-hexane : ethyl acetate=15:1) to obtain 2.08 g (yield 52%) of 2-(trans-1-hydroxy-2-nonenyl)-3-methyl-4-acetoxyquinoline.

MS m/e 341 (M+).
IR (neat) 3380, 2950, 1770, 1660, 1620, 1600, 1500, 1370, 1200 cm$^{-1}$.
NMR (CDCl$_3$).
$\delta$=0.86 (t, J=6Hz, 3H), 1.18-1.42 (m, 8H), 1.98-2.12 (m, 2H) 2.24 (s, 3H), 2.52 (s, 3H), 5.34 (d, J=7.8Hz, 1H), 5.45 (dd, J=16Hz, J=7.8Hz, 1H), 5.75 (bs, 1H), 5.86 (dt, J=16Hz, J=6.8Hz), 7.5-7.8 (m, 3H), 8.0-8.2 (m, 1H).

EXAMPLE 9

2-(trans-1-hydroxy-2-nonenyl)-3-methyl-4-quinolone [Compound (10)]

A solution of 502 mg (3.63 mmols) of potassium carbonate in 2 ml of water was added to a solution of 1.23 g (3.63 mmols) of 2 (trans-1-hydroxy-2-nonenyl)-3-methyl-4-acetoxyquinoline, 15 ml of water and 80 ml of methanol and stirred at room temperature for 10 minutes. After neutralization by addition of 1N hydrochloric acid, the solvent was distilled off under reduced pressure and 30 ml of chloroform was added to the resultant residue, followed by washing with water and drying with sodium sulfate. The solvent was distilled off under reduced pressure and the resultant residue was purified by silica gel column chromatography (Wako Gel C-200) (solvent: n-hexane : ethyl acetate=1:2) to obtain 746 mg (yield 69%) of 2-(trans-1-hydroxy-2-nonenyl)-3-methyl-4-quinolone.

Melting point 170°-171° C.
MS m/e 299 (M+).
NMR (CDCl$_3$). $\delta$=0.83 (t, J=7Hz, 3H), 1.1-1.4 (m, 8H), 1.76 (s, 3H), 1.9-2.1 (m, 2H), 4.92 (bs, 1H), 5.17 (d, J=6.5Hz, 1H), 5.46 (dd, J=16Hz, J=6.5Hz, 1H), 5.67 (dt, J=16Hz, J=7.3Hz, 1H), 7.03-7.10 (m, 1H), 7.21-7.34 (m, 1H), 7.35-7.48 (m, 1H), 8.21-8.31 (m, 1H), 9.11 (s, 1H).

EXAMPLE 10

2-(trans-1-nonenyl)-3-methyl-4-acetoxy-6-fluoroquinoline 0.29 ml of a hexane solution of 0.48 mmols of n-butyl lithium was added to a solution of 218 mg (0.48 mmols) of octyltriphenylphosphonium bromide in 3 ml of tetrahydrofuran and stirred at room temperature for 5 minutes. This solution was cooled to −78° C., after which 1.43 g (8 mmols) of hexamethylphosphorus triamide was added and stirred for 5 minutes, followed by further addition of 2 ml of a tetrahydrofuran solution of 98.8 mg (0.40 mmols) of 2-formyl-3-methyl-4-acetoxy-6-fluoroquinoline and stirring at −78° C. for 15 minutes and −42° C. for 30 minutes. The reaction solution was added to 20 ml of water and extracted with ethyl acetate, followed by washing with a saturated sodium chloride aqueous solution and drying with anhydrous sodium sulfate. After removal of the solvent by distillation under reduced pressure, the residue was purified by silica gel column chromatography (solvent n-hexane : ethyl acetate=30:1) to obtain 14 mg (yield 10 %) of 2-(trans-1-nonenyl)-3-methyl-4-acetoxy-6-fluoroquinoline.

NMR (CDCl$_3$).
$\delta$=0.89 (t, 3H, J=5Hz), 1.1-1.7 (m, 10H), 2.28 (S, 3H), 2.3-2.4 (m, 2H), 2.48 (S, 3H), 6.72 (d, 1H, J=15Hz), 6.87 (dt, 1H, J=6Hz, 15Hz), 7.1-7.5 (m, 2H), 7.99 (dd, 1H, J=5Hz, 9Hz).

EXAMPLE 11

2-(trans-1-nonenyl)-3-methyl-6-fluoro-4-quinolone 1.5 ml of an aqueous solution of 91 mg (0.66 mmols) of potassium carbonate was added to a solution of 226 mg (0.66 mmols) of 2-(trans-1-nonenyl)-3-methyl-4-acetoxyquinoline in 15 ml of methanol and stirred at room temperature for one hour. This solution was neutralized with 1N hydrochloric acid, after which the solvent was distilled off under reduced pressure, to which 10 ml of chloroform was added, followed by washing with water and drying with anhydrous sodium sulfate. The solvent was distilled off under reduced pressure and the resultant residue was purified by silica gel column chromatography (solvent: n-hexane : ethyl acetate=2:1) to obtain 160 mg (yield 80 %) of 2-(trans-1-nonenyl)-3 methyl-6-fluoro-4-quinolone.

Melting point 192°-193° C.
EI-MS 301 (M+).
NMR (CDCl$_3$).
$\delta$=0.83 (t, 3H, J=5Hz), 1.0-1.5 (m, 10H), 1.9-2.1 (m, 2H), 2.17 (s, 3H), 6.3-6.8 (m, 2H), 7.23 (dt, 1H, J=2Hz, 8Hz), 7.69 (dd, 1H, J=2Hz, 9Hz), 7.89 (dd, 1H, J=2Hz, 9Hz).

EXAMPLE 12

2-(trans-2-nonenyl)-3 methyl-4-acetoxy-6-fluoroquinoline .

5.99 ml of a pentane solution of 9.34 mmols of t-butyl lithium was added to 1.11 g (4.67 mmols) of trans-1-iodo-1-octene, 15 ml ether solution in an atmosphere of argon at −78° C. and stirred at the same temperature for 2 hours. 400 mg (2.10 mmols) of copper iodide was added to the reaction solution, after which it was heated up to −35° C. and stirred at the same temperature for 45 minutes. 941 mg (5.25 mmols) of hexamethylphosphorus triamide was added to the solution and stirred at —35° C. for 10 minutes, to which 10 ml of a tetrahydrofuran solution of 628 mg (1.75 mmols) of 2-iodomethyl-3-methyl-4 acetoxy-6-fluoroquinoline was added, followed by stirring at the same temperature for 30 minutes. The reaction solution was added to a solution of 2 ml of 1N hydrochloric acid and 100 ml of water, followed by filtration through Celite. The resultant filtrate was extracted with chloroform, washed with water and dried with anhydrous sodium sulfate. The solvent was distilled off under the reduced pressure and the residue was purified by silica gel column chromatography (solvent: n-hexane : ethyl acetate=15:1) to obtain 120 mg (yield 20 %) of 2-(trans-2-nonenyl)-3-methyl-4-acetoxy-6-fluoroquinoline.

NMR (CDCl$_3$).

$\delta$=0.83 (t, 3H, J=5Hz), 1.0-1.5 (m, 8H), 1.8-2.1 (m, 2H), 2.24 (s, 3H), 2.44 (s, 3H), 3.68 (d, 2H, J=5Hz), 5.3-5.8 (m, 2H), 7.1-7.5 (m, 2H), 7.99 (dd, 1H, J=5Hz, 9Hz).

EXAMPLE 13

2-(trans-2-nonenyl)-3-methyl-6-fluoro-4-quinolone

A solution of 24 mg (0.17 mmols) of potassium carbonate and 1 ml of water was added to a solution of 60 mg (0.17 mmols) of 2-(trans-2-nonenyl)-3-methyl-4-acetoxy-6-fluoroquinoline in 8 ml of methanol and stirred at room temperature for 10 minutes. This solution was neutralized with 1N hydrochloric acid, after which the solvent was distilled off under reduced pressure, followed by addition of 10 ml of chloroform, washing with water and drying with anhydrous sodium sulfate. The solvent was distilled off under reduced pressure and the resultant residue was purified by silica gel column chromatography (solvent: n-hexane : ethyl acetate=1:1) to obtain 46 mg (yield 87 %) of 2-(trans-2-nonenyl)-3-methyl-6-fluoro-4-quinolone.

Melting point 214°-215° C.

EI-MS 301 (M+).

NMR (CDCl$_3$).

$\delta$=0.85 (t, 3H, J=7Hz), 1.20-1.32 (m, 8H), 1.97-2.03 (m, 2H), 2.18 (s, 3H), 3.51 (d, 2H, J=5.9 Hz), 5.51 (dt, 1H, J=5.9 Hz, 15.2 Hz), 5.60 (dt, 1H, J=6.3 Hz, 15.2 Hz), 7.27-7.32 (m, 1H), 7.60 (dd, 1H, J=4.5 Hz, 9.2 Hz), 7.98 (dd, 1H, J=3.0 Hz, 9.2 Hz), 11.0 (s, 1H).

EXAMPLE 14

2-(1-hydroxy-2-nonynyl)-3-methyl-4-acetoxy-6-fluoroquinoline 1.32 ml of a hexane solution of 2.16 mmols of n-butyl lithium was added to a solution of 238 mg (2.16 mmols) of 1-octyne and 5 ml of tetrahydrofuran in an atmosphere of nitrogen at 0° C. and stirred at the same temperature for 15 minutes. The reaction solution was cooled to −78° C. to which a solution of 10 ml of tetrahydrofuran of 445 mg (1.80 mmols) of 2-formyl-3-methyl-4-acetoxy-6-fluoroquinoline was added, followed by heating gradually to room temperature and stirring at room temperature for 1 hour. The reaction solution was poured into 50 ml of water, extracted with ethyl acetate and dried with sodium sulfate. The solvent was distilled off under reduced pressure and the resultant residue was purified by silica gel column chromatography (Wako gel C-200) (solvent: n-hexane ethyl acetate=5:1) to obtain 349 mg (yield 54 %) of 2-(1-hydroxy-2-nonynyl)-3-methyl-4-actoxy-6-fluoroquinoline.

NMR (CDCl$_3$).

$\delta$=0.83 (t, 3H, J=5Hz), 1.0-1.7 (m, 8H), 2.0-2.2 (m, 2H), 2.33 (s, 3H), 2.49 (s, 3H), 5.4-5.8 (m, 2H), 7.1-7.5 (m, 2H), 8.02 (dd, 1H, J=5Hz, 9Hz).

EXAMPLE 15

2-(1-hydroxy-2-nonynyl)-3-methyl-6-fluoro-4-quinolone

A solution of 135 mg (0.978 mmols) of potassium carbonate in 1 ml of water was added to a solution of 349 mg (0.978 mmols) of 2-(1-hydroxy-2-nonynyl)-3-methyl-4-acetoxy-6-fluoroquinoline, 20 ml of methanol and 2 ml of water and stirred at room temperature for 10 minutes. After neutralization with 1N hydrochloric acid, the solvent was distilled off under reduced pressure, followed by addition of 20 ml of chloroform to the resultant residue, washing with water and drying with sodium sulfate. The solvent was distilled off under reduced pressure, followed by purification by silica gel column chromatography (Wako gel C-200) (solvent: n-hexane : ethyl acetate=1:1) to obtain 183 mg (yield 59 %) of 2-(1-hydroxy-2-nonynyl)-3-methyl-6-fluoro-4-quinolone.

Melting point 153°-154° C.

EI-MS 315 (M+).

NMR (CD$_3$OD).

$\delta$=0.83 (t, 3H, J=5Hz), 1.1-1.7 (m, 8H), 2.17 (s, 3H), 2.2-2.5 (m, 2H), 3.30 (bs, 1H), 5.66 (t, 1H, J=2Hz), 7.41 (ddd, 1H, J=3Hz, 8Hz, 9Hz), 7.7-7.9 (m, 2H).

EXAMPLE 16

2-(trans-1-hydroxy-2-nonenyl)-3-methyl-4-acetoxy-6-fluoroquinoline 10.8 ml of an n-hexane solution of 10.8 mmols of diisobutylaluminium hydride was added to a solution of 1.31 g (11.9 mmols) of 1-octyne in 20 ml of n-hexane in an atmosphere of nitrogen and stirred at 50° C. for 2 hours. The reaction solution was cooled to −78° C., to which a solution of 2.22 ml (9.00 mmols) of 2-formyl-3-methyl-4-acetoxy-6-fluoroquinoline in 30 ml of tetrahydrofuran was added. The reaction temperature was raised from −78° C. to room temperature and the reaction solution was stirred at room temperature for 30 minutes. The reaction solution was added to 100 ml of water and filtered through Celite, followed by extraction with ethyl acetate, washing with water and a saturated sodium chloride aqueous solution, and drying with anhydrous magnesium sulfate. The solvent was distilled off under reduced pressure and the resultant residue was purified by silica gel column chromatography (solvent: n-hexane ethyl acetate=8:1) to obtain 1.86 g (yield 58 %) of 2-(trans-1-hydroxy-2-nonenyl)-3-methyl-4-acetoxy-6-fluoroquinoline.

NMR (CDCl$_3$).

$\delta$=0.83 (t, 3H, J=5Hz), 1.0-1.6 (m, 8H), 2.20 (s, 3H), 2.45 (s, 3H), 5.1-5.55 (m, 3H), 5.6-6.0 (m, 1H), 7.2-7.5 (m, 2H), 8.01 (dd, 1H, J=5Hz, 9Hz).

EXAMPLE 17

2-(trans-1-hydroxy-2-nonenyl)-3-methyl-6-fluoro-4-quinolone

A solution of 715 mg (5.18 mmols) of potassium carbonate in 3 ml of water was added to a solution of 1.86 g (5.18 mmols) of 2-(trans-1-hydroxy-2-nonenyl)-3-methyl-4-acetoxy-6-fluoroquinoline, 50 ml of methanol and 2 ml of water and stirred at room temperature for 10 minutes. After neutralization by addition of 1N hydrochloric acid, the solvent was distilled off under reduced pressure and 30 ml of chloroform was added to the resultant residue, followed by washing with water and drying with anhydrous sodium sulfate. The solvent was distilled off under reduced pressure and the resultant residue was purified by silica gel column chromatography (solvent: chloroform : methanol=40:1) to obtain 1.19 g (yield 72 %) of 2-(trans-1-hydroxy-2-nonenyl)-3-methyl-6-fluoro-4-quinolone.

Melting point 163°–164° C.
EI-MS 317 (M+).
NMR (CDCl$_3$).
$\delta$=0.83 (t, 3H, J=7Hz), 1.1–1.4 (m, 8H), 1.85 (s, 3H), 1.9–2.1 (m, 2H), 4.89 (bs, 1H), 5.27 (bs, 1H), 5.48 (dd, 1H, J=6.5 Hz, 15.4 Hz), 5.73 (dt, 1H, J=6.8 Hz, 15.4 Hz), 7.1–7.3 (m, 2H), 7.88 (dd, 1H, J=3Hz, 9Hz), 9.35 (s, 1H).

PREPARATORY EXAMPLE 1

2-formyl-3-methyl-4-acetoxyquinoline

A solution of 4.30 g (20.0 mmols) of 2,3-dimethyl-4-acetoxyquinoline, 2.44 g (22.0 mmols) of selenium dioxide, 8 ml of water and 80 ml 1,4-dioxane was refluxed for 3 hours. The solvent was distilled off under reduced pressure, after which 100 ml of chloroform was added, followed by washing with a saturated sodium hydrogencarbonate aqueous solution and then with water, and drying with sodium sulfate. The solvent was distilled off under reduced pressure and the resultant crude product was purified by silica gel column chromatography (Wako Gel C-200) (solvent: n-hexane : ethyl acetate=10:1) to obtain 2.40 g (yield 52%) of 2-formyl-3-methyl-4-acetoxyquinoline.

Melting point 132°–133° C.
NMR (CDCl$_3$).
$\delta$=2.52 (s, 3H), 2.59 (s, 3H), 7.5–8.3 (m, 4H), 10.3 (s, 1H).

PREPARATORY EXAMPLE 2

2-chloromethyl-3-methyl-4-acetoxyquinoline

A solution of 4.95 g (23.0 mmols) of 2, 3-dimethyl-4-acetoxyquinoline, 4.76 g (27.6 mmols) of m-chloroperbenzoic acid and 50 ml of methylene chloride was stirred at room temperature for 2 hours, to which was subsequently added 79.4 mg (4.6 mmols) of m-chloroperbenzoic acid, followed by stirring at the same temperature for 3 hours. The reaction solution was washed with a sodium hydrogensulfite aqueous solution, a saturated sodium hydrogencarbonate and finally a saturated sodium chloride aqueous solution, followed by drying with sodium sulfate. The solvent was distilled off under reduced pressure to obtain 5.42 g of a crude product of 2, 3-dimethyl-4-acetoxyquinoline oxide.

A solution of 1.38 g (9.04 mmols) of phosphorus oxychloride in 5 ml of methylene chloride and a solution of 913 mg (9.04 mmols) of triethylamine in 5 ml of methylene chloride were, respectively, dropped almost simultaneously in 15 minutes into a solution of 1.85 g (8.00 mmols) of the crude product of 2, 3-dimethyl-4-acetoxyquinoline oxide in 5 ml of methylene chloride, followed by stirring at room temperature for 10 minutes. The reaction solution was washed with a saturated sodium hydrogencarbonate aqueous solution and saturated sodium chloride aqueous solution, and dried with sodium sulfate. The solvent was distilled off under reduced pressure to obtain a crude product, followed by purification by silica gel column chromatography (Wako (solvent: n-hexane : ethyl acetate=5:1) to obtain 700 mg (yield 36%) of 2-chloromethyl-3-methyl-4-acetoxyquinoline.

Melting point 108°–109° C.
NMR (CDCl$_3$).
$\delta$=2.40 (s, 3H). 2.49 (s, 3U), 4.83 (s. 2H), 7.3–8.0 (m, 4H).

The antagonistic action on leukotriene D$_4$ and the mouse life-prolonging action under reduced pressure of the compounds of the invention are described hereunder.

TEST EXAMPLE 1

Test of Antagonistic Action on Leukotriene D$_4$
a) Test method
Pieces of the ileum of guinea pig were used and an inhibition rate for their contraction caused by 10 ng/ml of leukotriene D$_4$ was determined as 2 mg/ml of a test sample were added.
b) Test samples
Compounds (3), (4) and (6) obtained in Examples.
c) Results
The results are shown in Table 1.

TABLE 1

| Test Sample | Antagonism on Leukotriene D$_4$ |
|---|---|
| Compound (3) | 100% |
| Compound (4) | 85% |
| Compound (6) | 90% |

As apparent from the above results, the compounds of the invention have significant antagonistic action on leukotriene D$_4$ and can suppress the contraction of the organ. Leukotriene D$_4$ is a substance which is released in allergic diseases. With asthma, for example, it has the action of contracting the bronchial tube and the compounds of the invention are thus effective in suppressing a spasm of asthma.

TEST EXAMPLE 2

Mouse Life-Prolonging Test Under Reduced Pressure
a) Test method
Groups of mice, each group consisting of three mice, were intravenously dosed with 50 mg of each test sample. After 30 minutes, the mice were placed in a cage which was reduced to 20 mmHg to measure surviving time (in seconds). A group of mice which were not dosed with any test sample were provided as a control.
b) Test samples
Compounds (3), (4) and (6) in Examples.
c) Results
The results are shown in Table 2.

TABLE 2

| Test Sample | Mouse Surviving Time (seconds) |
|---|---|
| Compound (3) | 210 |
| Compound (4) | 180 |
| Compound (6) | 190 |
| Control | 80 |

As apparent from the above results, the compounds of the invention can increase the blood flow to the brain and can significantly prolong the brain death time in an anoxic condition. Accordingly, they are effective for curing asphyxiation or brain diseases such as carbon monoxide intoxication.

The novel 2, 3-disubstituted-4-hydroxyquinoline derivatives of the invention have both an antagonistic action on leukotriene $D_4$ and the action of increasing the blood flow to the brain from the heart. Hence, these compounds effectively act on the immune system and the blood flow of the heart which are important for the life maintenance of mammals including human beings and are very effective for curing immunological diseases and brain diseases.

What is claimed is:

1. A 2,3-disubstituted-4-hydroxyquinoline compound, which is 2-(cis-1-nonenyl)-3-methyl-4-quinolinol.

* * * * *